(12) United States Patent
Berger et al.

(10) Patent No.: US 7,089,050 B2
(45) Date of Patent: Aug. 8, 2006

(54) METHOD AND APPARATUS FOR MEASURING BLADDER ELECTRICAL ACTIVITY TO DIAGNOSE BLADDER DYSFUNCTION

(76) Inventors: Yitzhak Berger, 465 Overhill Rd., South Orange, NJ (US) 07079; Issac P. Baldar, 24 Goodhart Dr., Livingston, NJ (US) 07039

( * ) Notice: Subject to any disclaimer, the term of this patent is extended or adjusted under 35 U.S.C. 154(b) by 459 days.

(21) Appl. No.: 10/662,729

(22) Filed: Sep. 15, 2003

(65) Prior Publication Data

US 2005/0059900 A1 Mar. 17, 2005

(51) Int. Cl.
*A61B 5/04* (2006.01)

(52) U.S. Cl. ............................................ 600/546

(58) Field of Classification Search ............... 600/546, 600/591, 547, 554, 587, 595, 300; 607/138
See application file for complete search history.

(56) References Cited

U.S. PATENT DOCUMENTS 4,088,125 A * 5/1978 Forgione et al. ............ 600/547
5,776,073 A * 7/1998 Garfield et al. ............. 600/546

* cited by examiner

*Primary Examiner*—Max F. Hindenburg
*Assistant Examiner*—Brian Szmal
(74) *Attorney, Agent, or Firm*—Epstein Drangel Bazerman & James

(57) ABSTRACT

A method of diagnosing bladder pathology uses Vesico Internal Sphincter ElectroMyogram (VISEMG) waveforms obtained from a plurality of VISEMG electrodes disposed on a patient. The VISEMG waveforms are converted to noninvasive (NI) urodynamic graphs. Further, a programmed computer assesses the condition of the bladder based on the VISEMG waveforms. The method does not require traditional urodynamics or any other invasive procedure. An apparatus to perform the inventive method uses a plurality of VISEMG electrodes placed on the patient. Each electrode signal is amplified and filtered and converted to a digital signal. A computer converts the digital signals (the VISEMG waveforms) to NI urodynamic graphs. Any combination of the VISEMG waveforms, the NI urodynamic graphs, and the condition of the bladder based on the VISEMG waveforms can then be shown on a display screen.

15 Claims, 14 Drawing Sheets

METHOD AND APPARATUS FOR MEASURING BLADDER ELECTRICAL ACTIVITY TO DIAGNOSE BLADDER DYSFUNCTION

FIELD OF THE INVENTION

This invention relates to a method and apparatus to diagnose bladder pathology from surface electrode potentials, and more specifically to a method and apparatus to convert surface potential measurements into graphs similar to those obtained by conventional invasive urodynamic testing. The resulting non-invasive urodynamic graphs can then be used to diagnose bladder pathology.

BACKGROUND OF THE INVENTION

The bladder collects and stores urine from the kidneys and allows for discharge of the urine. The two bladder functions are controlled by the sympathetic and the parasympathetic autonomic neurological systems, and these are coordinated by the brain via the spinal cord.

The first function is to store urine in a low pressure environment without leakage. The detrusor, or bladder muscle, maintains low pressure within the bladder cavity during the storage phase. A sympathetic input prevents an increase of intravesical pressure during the accumulation of urine, and it inhibits bladder contraction. It also activates the internal sphincteric muscle (bladder neck) thus providing continence of urine.

For evacuation of the urine (micturition), the parasympathetic system causes the contraction of the detrusor muscle and the relaxation of the internal sphincter (bladder neck), thus permitting an unobstructed flow of urine.

Patients exhibit urinary symptoms due to various neurogenic (functional) or non neurogenic (anatomic) causes such as bladder outlet obstruction, overactive bladder, poor urethral support due to abnormal relaxation of the pelvic floor musculature, or sphincteric incompetence.

Urodynamic testing is a set of standard diagnostic tests used to study various urinary disorders. The testing typically includes bladder and abdominal pressure measurements, uroflows, electromyographic (EMG) signals of the external sphincter and the pelvic floor muscles, and radiographic images of the internal structure of the bladder's cavity and urethra. (See: *The Bladder*, Fitzpatrick, Krane, *Urodynamic Studies*, chapter 6, Y. Berger, pages 119–128, Churchill Livingstone, 1995; *Outcomes and Obstacles of urodynamics, Contemporary Urology*, Y. Berger, pages 15–31, August 1995 both of which are incorporated by reference herein). Urodynamic testing, while supplemented by electrical measurements and radiology, is primarily a system of mechanical tests. Pressure measurements are obtained via catheters that are inserted into the bladder (for intra vesical and intraabdominal pressure recordings and urethral profile pressure) or rectum (for intra abdominal pressure recordings). Uroflows are graphical and numerical data that record the stream of urine (typically measured in milliliters (ml)/sec). The EMG electrophysiological recordings are obtained from the striated external sphincteric and pelvic floor muscles and are obtained with patches (electrodes) or needles. And finally, radiographic imaging of the internal structure and contour of the bladder and its outlet can be obtained via fluoroscopic or still images during the phases of bladder storage and micturition. These measurements have standardized values that are representative of normal or abnormal bladder function.

Urodynamics, however, does not record the electromyographic activity of the smooth muscles of either the bladder (detrusor) or the internal sphincteric muscle (bladder neck). These muscles are subjected to the input of the autonomic (sympathetic and parasympathetic) neurological system. Therefore, the current evaluation of bladder function as displayed by the traditional urodynamic measurements may reflect only the outcome of mechanical pressure changes (normal or abnormal) that are the results of electrophysiological (neurogenic or myogenic) activities (normal or abnormal) that are not being assessed. For example, in the case of overactive bladder (OAB), the urodynamics will reveal evidence of involuntary detrusor contractions (IDC's) measured as abrupt bladder pressure elevations, but not disclose the cause of the IDC's. In addition, the urodynamic tests are invasive in nature, and they cannot be performed in an ambulatory setting. Urodynamic testing must be done in a clinic (office or hospital), the tests cause patient discomfort, and the data produced is artificial from a non-natural environment. Nonetheless urodynamic tests present results, primarily in the form of urodynamic graphs, that doctors and urologists are accustomed to employing in diagnosing bladder pathology.

Accordingly there is a need for a noninvasive method of measuring bladder activity for diagnosing bladder pathology and advantageously presenting the measurements in the urodynamics format familiar to doctors and urologists.

SUMMARY OF THE INVENTION

A method of diagnosing bladder pathology uses Vesico Internal Sphincter ElectroMyoGram (VISEMG) waveforms obtained from a plurality of VISEMG electrodes disposed on a patient. The VISEMG waveforms are converted to noninvasive (NI) urodynamic graphs. Further, a programmed computer assesses the condition of the bladder based on the VISEMG waveforms. The method does not require traditional urodynamics or any other invasive procedure.

An apparatus to perform the inventive method uses a plurality of VISEMG electrodes placed on the patient. Each electrode signal is amplified and filtered and converted to a digital signal. A computer converts the digital signals (the VISEMG waveforms) to NI urodynamic graphs. Any combination of the VISEMG waveforms, the NI urodynamic graphs, and the condition of the bladder based on the VISEMG waveforms can then be shown on a display screen.

DRAWINGS

The advantages, nature and various additional features of the invention will appear more fully upon consideration of the illustrative embodiments now to be described in detail in connection with the accompanying drawings. In the drawings.

It is to be understood that the drawings are for the purpose of illustrating the concepts of the invention are not to scale.

DETAILED DESCRIPTION

The description is divided into two parts. Part I introduces the inventive methods and apparatus and explains the significance of the invention as a new diagnostic technique in urology. Part II presents the apparatus in more detail, including engineering aspects related to the hardware and software. Appendix I describes additional exemplary display screens according to one embodiment of the apparatus.

PART I: BLADDER SPHINCTER AND DETRUSOR MUSCLE VISEMG

Figure 1:
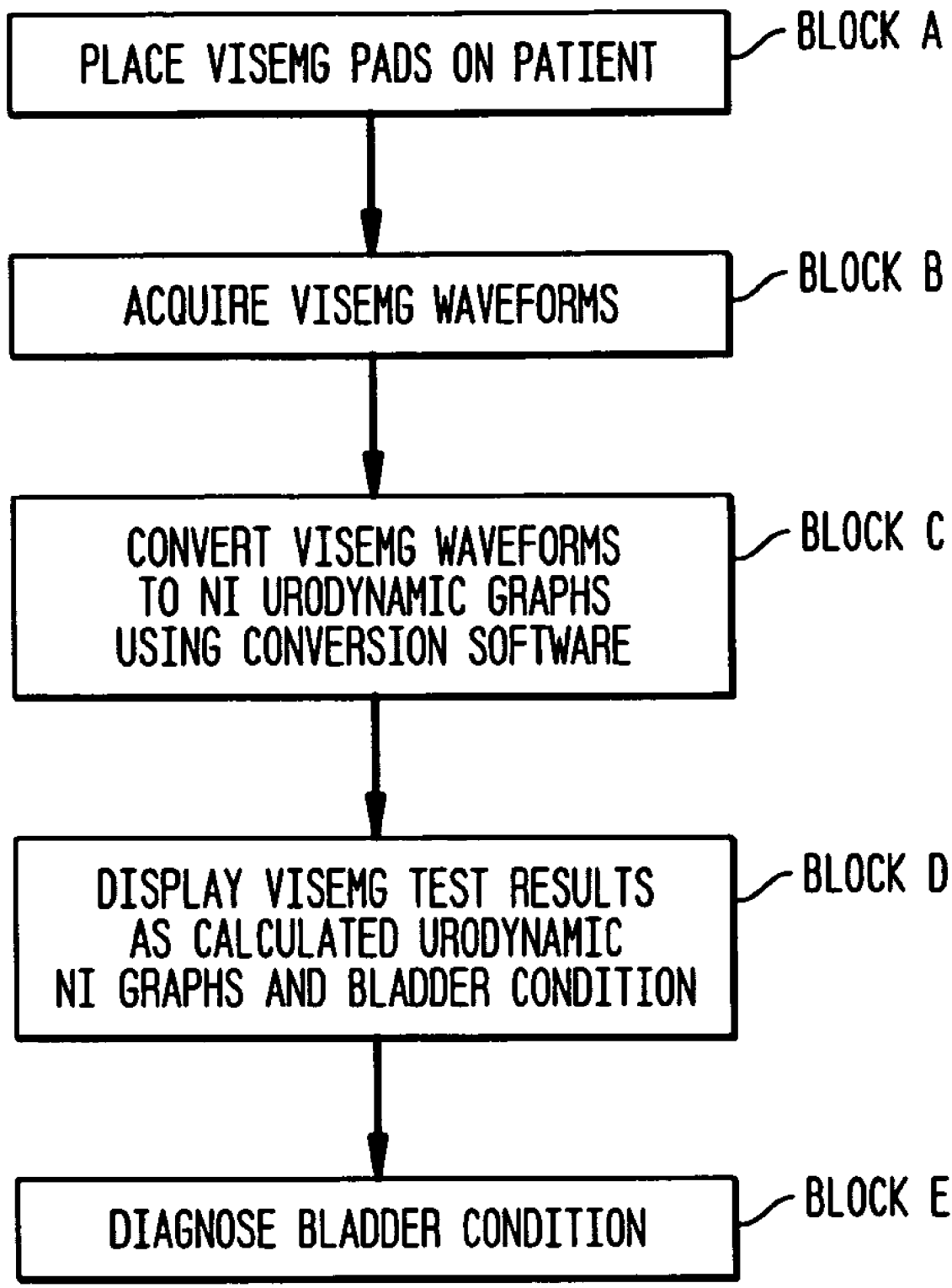
FIG. 1 is a block diagram showing a first embodiment of the inventive method.

A first embodiment of the inventive method is shown in FIG. 1. In this non-invasive diagnostic test, Vesico Internal Sphincter ElectroMyogram (VISEMG) electrodes are placed on the patient (Block A). The VISEMG electrodes are surface electrodes that record electromyographic signals from the bladder and internal sphincter muscles. The VISEMG waveforms are then acquired from the electrodes (Block B).

The VISEMG waveforms are converted to non-invasive (NI) urodynamic graphs (Block C). NI urodynamic graphs are graphs that are calculated from the VISEMG waveforms. The calculations are done by conversion software or in hardware.

The results of the test are displayed as NI urodynamic graphs along with information on bladder condition as derived from the VISEMG waveforms (Block D). A clinician then can make a diagnosis based at least in part on the displayed test results (Block E).

Figure 2:
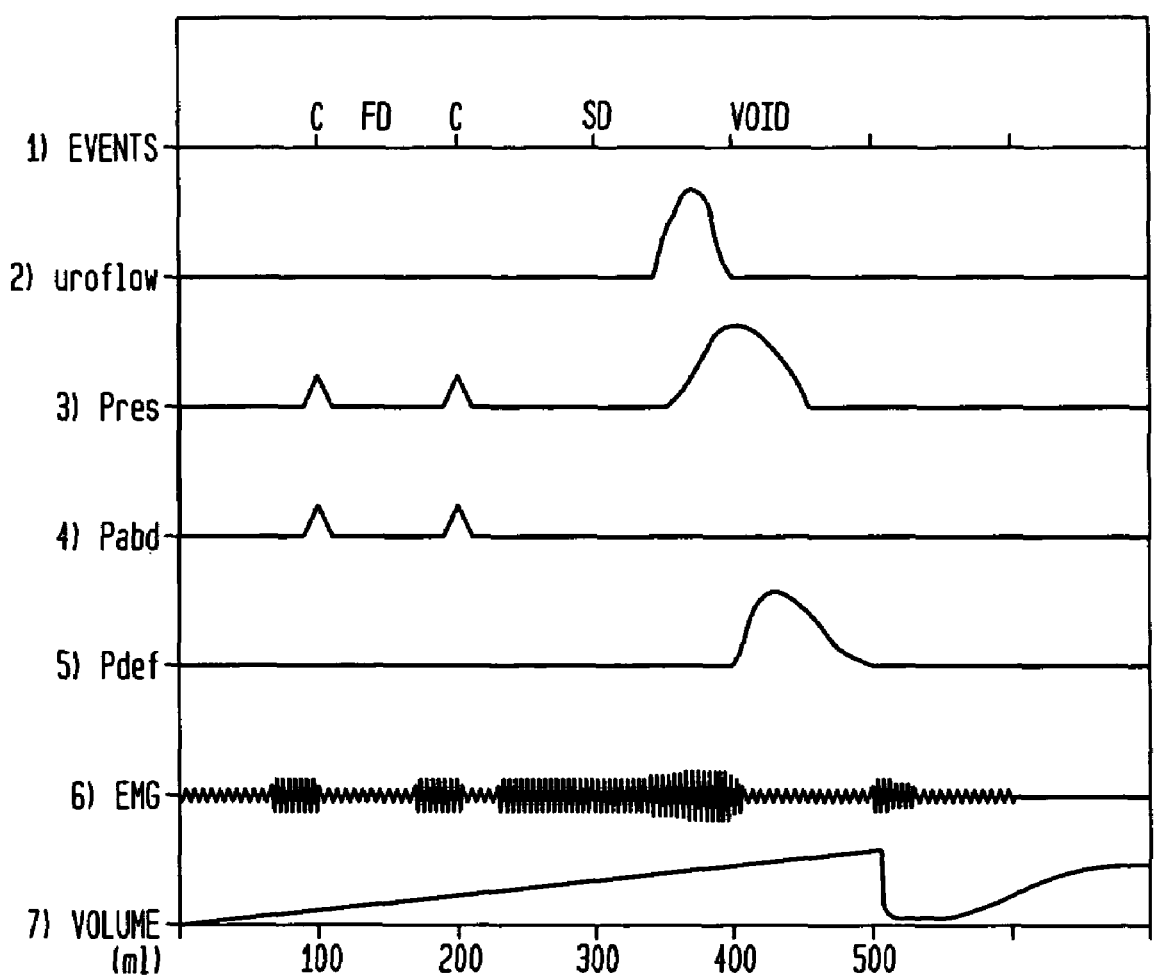
FIG. 2 shows one embodiment of a display screen according to the method of FIG. 1.

The inventive method is completely non-invasive. The displayed NI urodynamic graphs are calculated data and can be clinically used similar to traditional urodynamic studies. The diagnostic method does not need to perform any of the traditional urodynamic tests. The medical community is already familiar with the interpretation of traditional Urodynamics and NI Urodynamics will provide diagnostic information similar to traditional urodynamics. Therefore, this will facilitate the diagnostic utilization of NI urodynamics in the clinical management of bladder conditions. FIG. 2 shows an exemplary display screen according to the method of FIG. 1.

The reference numbers in FIG. 2 are defined as follows: 1) Events—Patient's sensation with bladder filling—a) ES, first cough; b) c cough; c) ED—1st desire; d) SD—strong desire; e) void—voiding. 2) uroflow in mi/sec. 3) Pres—intravesical pressure (mm H20). 4) Pabd—intraabdominal pressure. 5) Pdet—subtracted—true detrusor pressure. 6) EMG—electromyography of external sphincter. 7) volume (in ml)—volume of fluid within the bladder.

Figure 3:
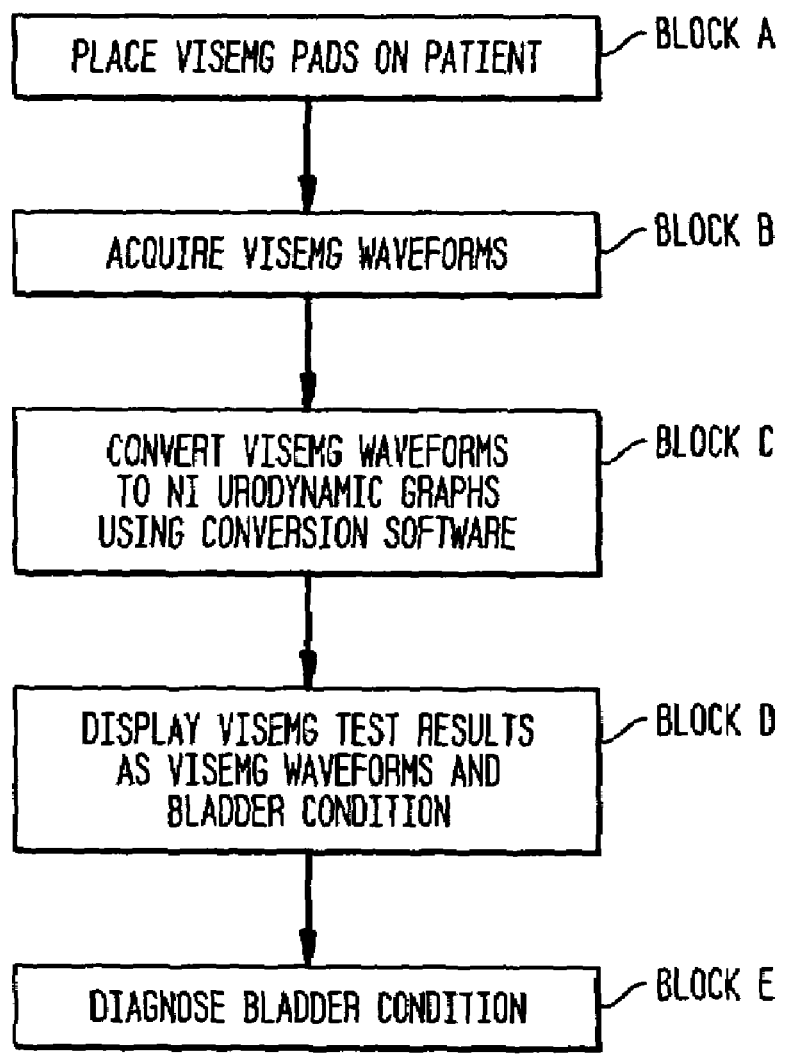
FIG. 3 is a block diagram showing a second embodiment of the inventive method.
Figure 4:
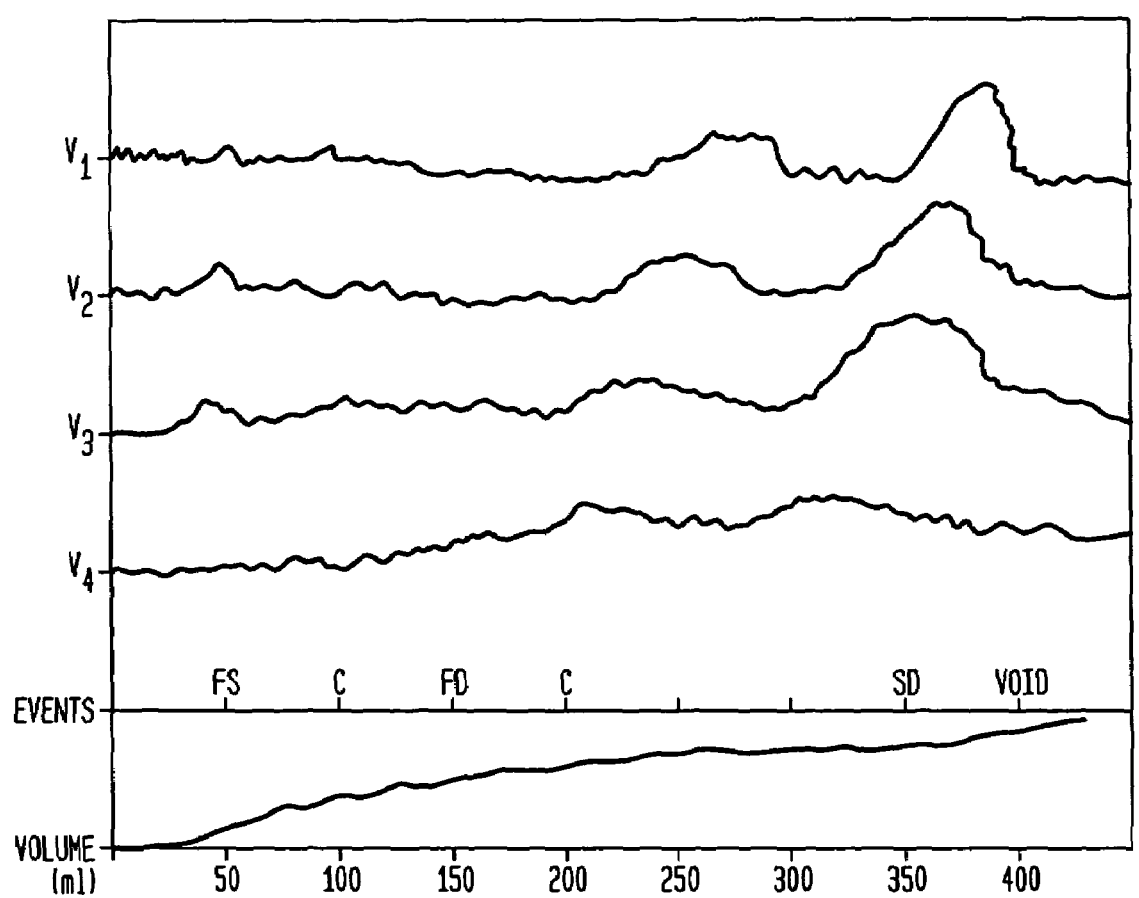
FIG. 4 shows one embodiment of a display screen according to the method of FIG. 3.
Figure 5:
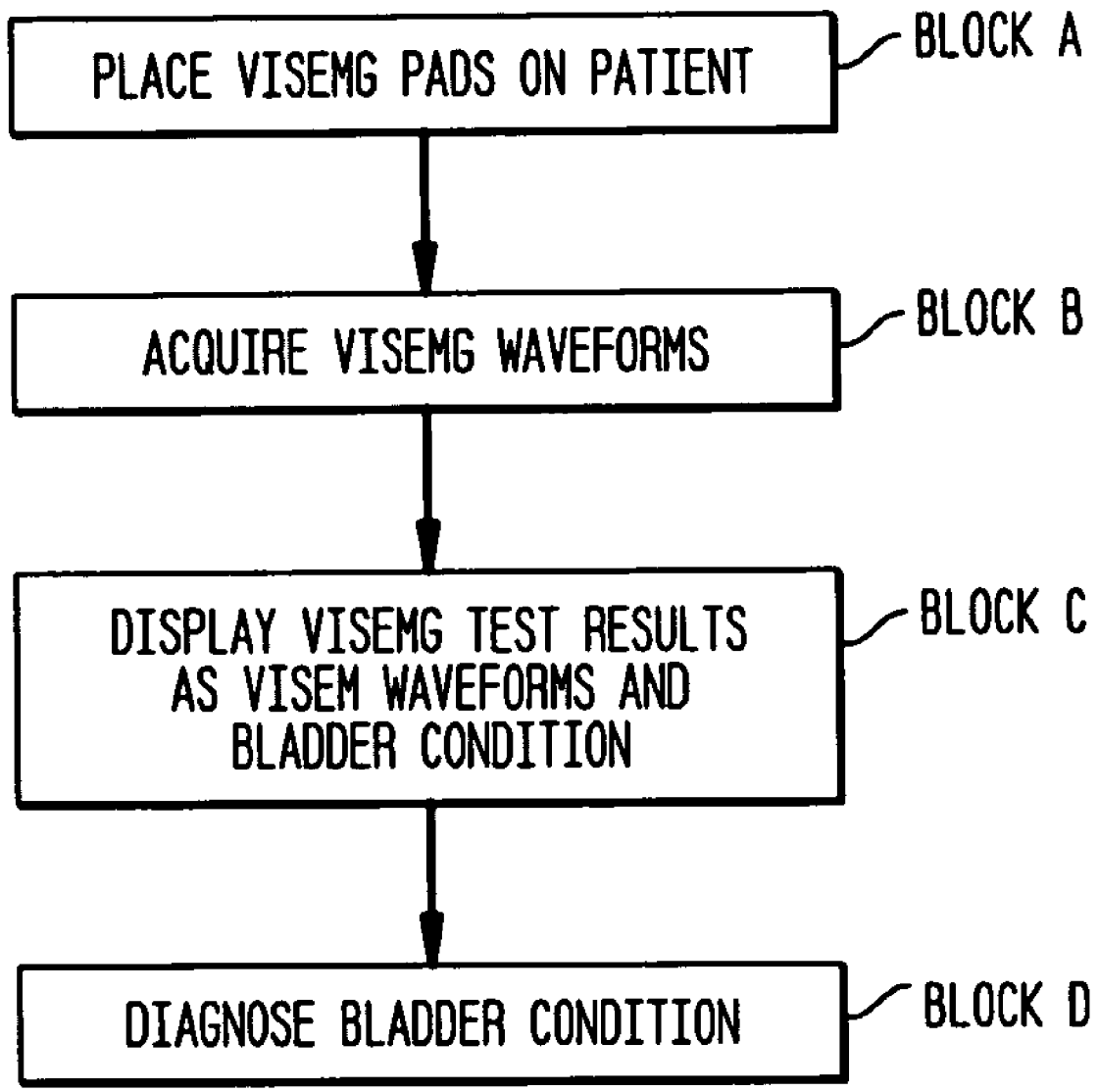
FIG. 5 is a block diagram showing a third embodiment of the inventive method.

As clinicians become better versed in the interpretation of VISEMG waveforms, it can be advantageous to directly display the VISEMG waveforms. This method is illustrated in the block diagram of FIG. 3. Only Block D differs where now the VISEMG waveforms are displayed instead of the NI urodynamic waveforms. FIG. 4 shows an exemplary display screen according to the method of FIG. 3.

The displayed VISEM waveforms are defined as follows: V1—right lower abdomen to suprapubic. V2—right lower abdomen to suprapubic. V3—subumbilical to suprapubic. V4—subumbilical to suprapubic.

In another embodiment of the invention, the NI urodynamic graphs can be simultaneously displayed on the display screen. Alternatively, displays having only one of the displays, or various combinations of the VISEMG waveforms, the NI urodynamic graphs, and the information on bladder condition can be displayed on individual screens. The NI urodynamics are the calculated outcome of the VISEMG waveforms translated to various clinical conditions.

Figure 6:
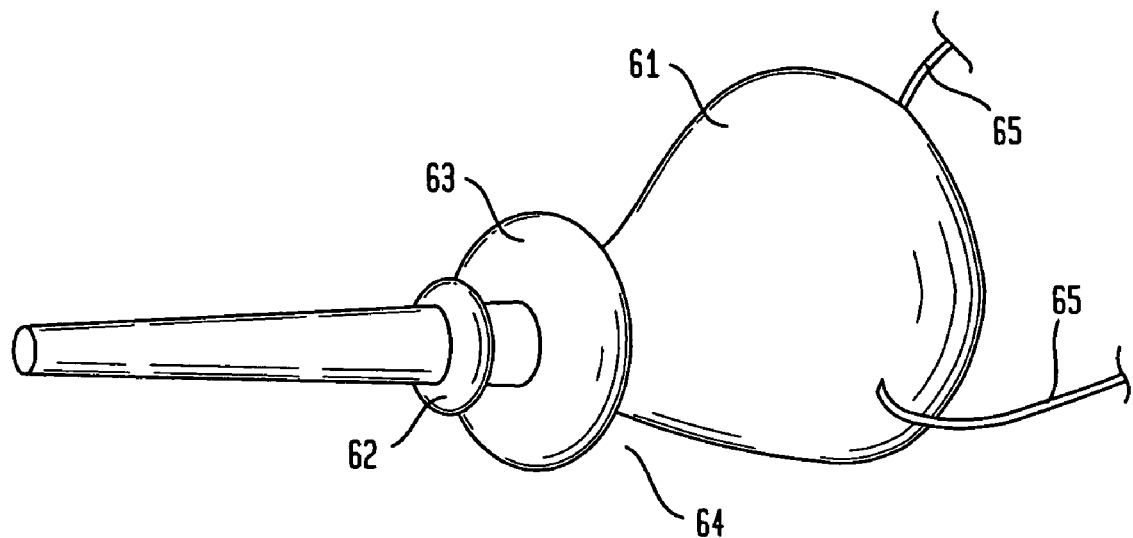
FIG. 6 shows a diagram of male bladder showing detrusor muscle, and internal and external sphincter muscles.
Figure 7:
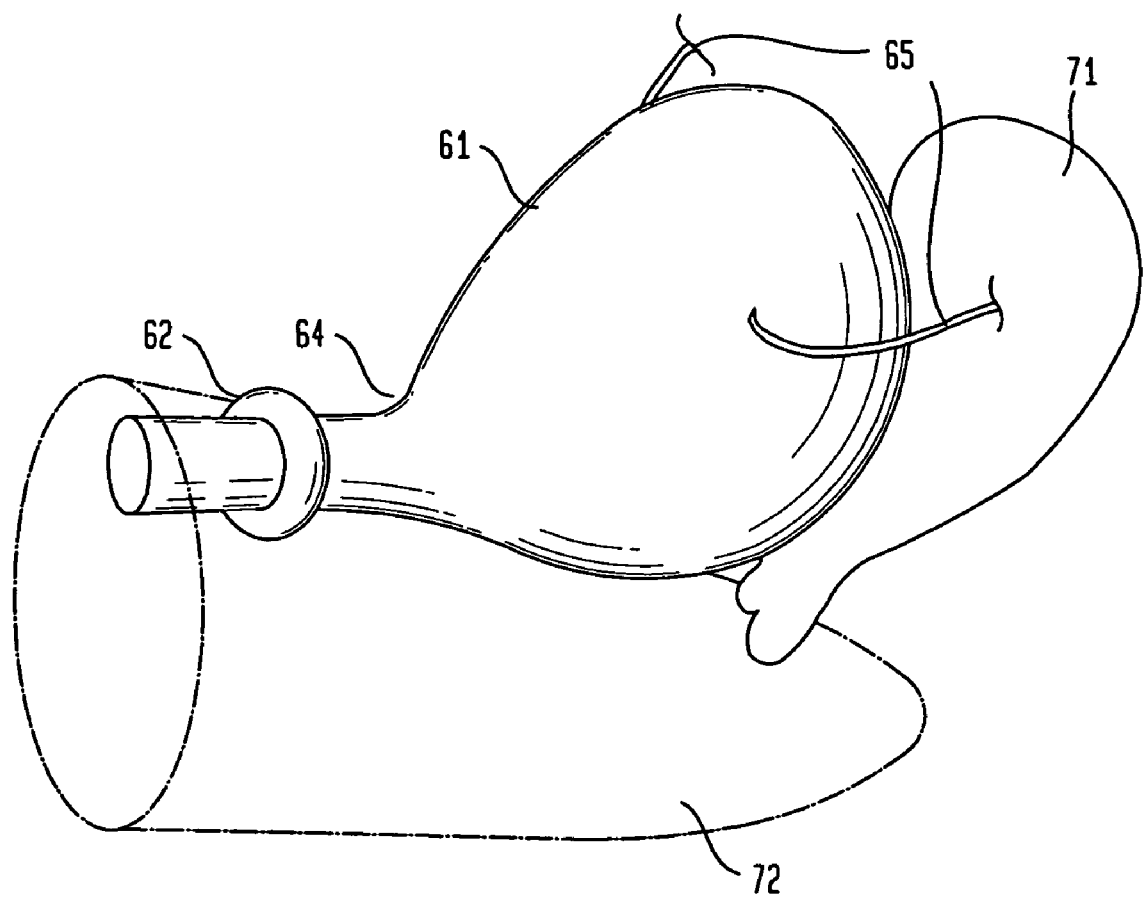
FIG. 7 shows a diagram of female bladder showing detrusor muscle, and internal and external sphincter muscles.
Figure 8:
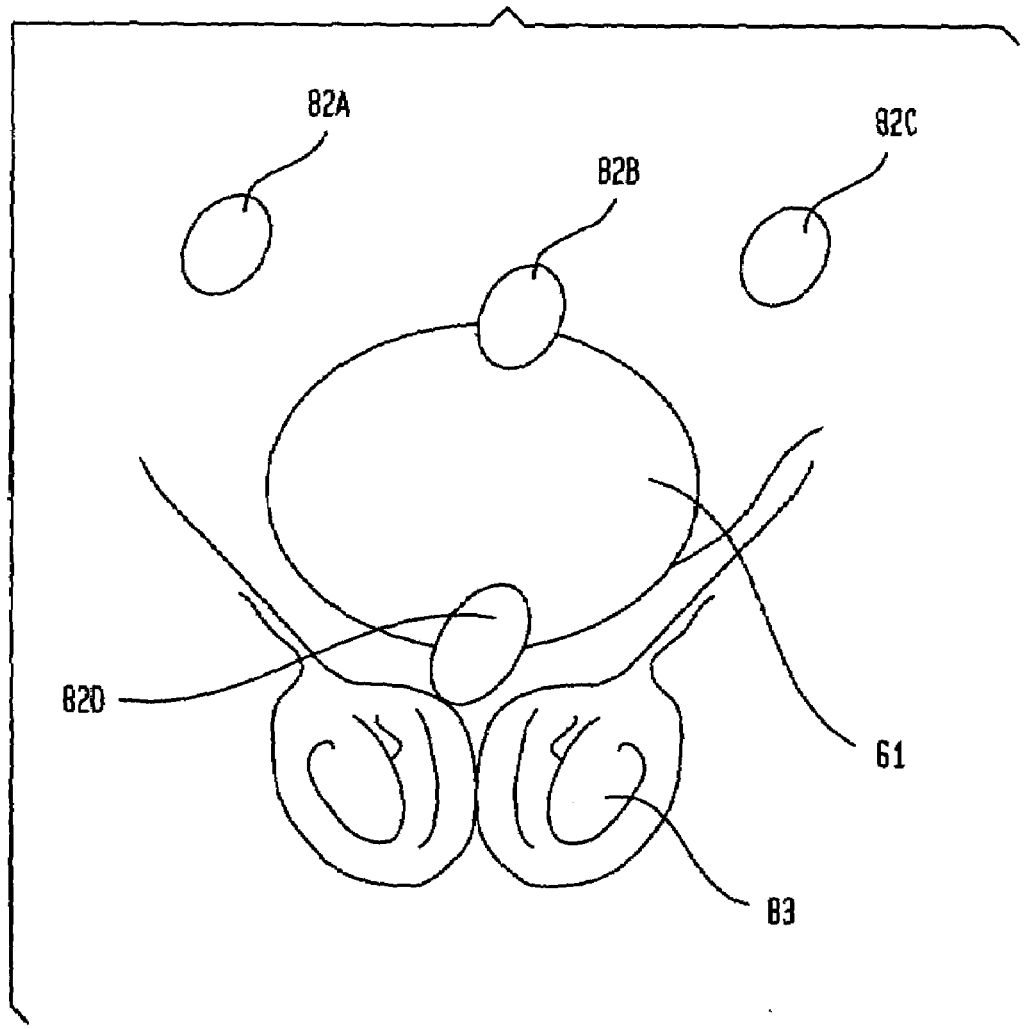
FIG. 8 shows an exemplary placement of VISEMG patches (electrodes)

The VISEMG method comprises affixing a set of surface probes (patches) to on the patient's body over the lower abdomen. The patches (surface electrodes) can pick up the VISEMG signals from the bladder detrusor and sphincter muscles. In order to better understand the bladder muscle signals of interest, FIGS. 6 and 7 show diagrams of the male and female bladders 61 respectively. VISEMG waveforms can be obtained from the external sphincter 62, the internal sphincter 64 (hidden from view) at the "bladder neck", and the detrusor muscle shown as the wall of bladder 61. The bladder cavity fills from ureters 65. FIG. 7, the female bladder, also shows the vagina 72 and uterus 71. Patches can be applied to the surface of the patient in the suprapubic and perineal regions. An exemplary placement of the patches 82 is shown in FIG. 8 with respect to pelvic bone 83 and bladder 61 as shown in a partial cutaway view of the abdomen near the bladder. The patches are right lateral (Rt) 82a, subumbilical (Su) 82b, left lateral (Lt) 82c, and suprapubic (Sp) 82d. Exemplary vectors (differential or action potentials) that can be used to generate VISEMG waveforms are $V_1$=Rt to Sp, $V_2$=Lt to Sp, $V_3$=Su to Sp, $V_4$=Rt to Su, and $V_5$=Rt to Su.

PART II: APPARATUS HARDWARE AND SOFTWARE

Figure 9:
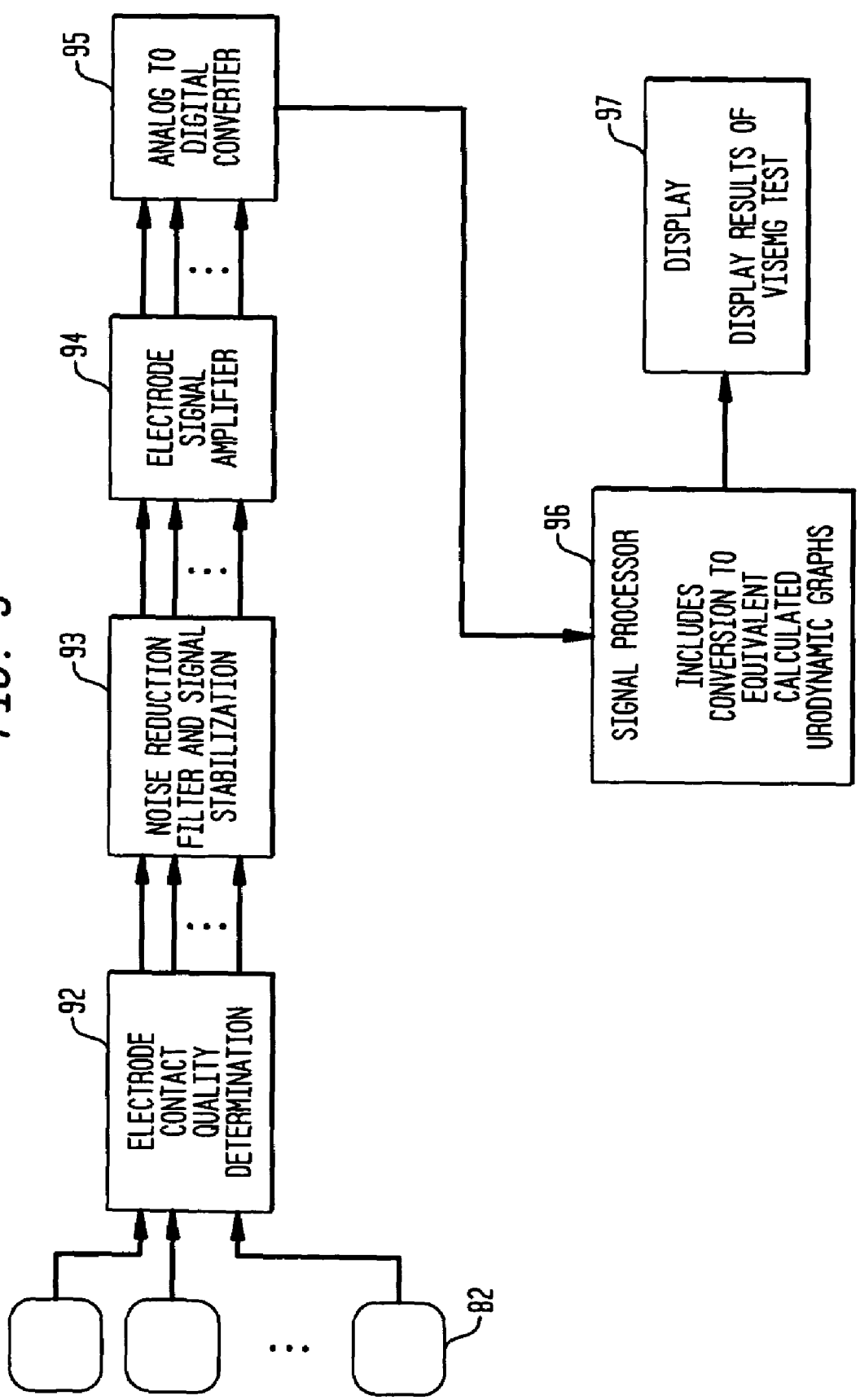
FIG. 9 shows an electronic block diagram of apparatus to perform the inventive method.

A block diagram of the apparatus is shown in FIG. 9. Recording electrodes (patches) 82 can be placed at various points on a patient's abdominal surface. The electrodes are electrically coupled to electrode contact and quality determining circuit 92 that optionally monitors electrode 82 contact quality with the patient and reports that quality to signal processor computer 96, or another control computer in the apparatus to provide control and user interface functions (link and optional user interface computer not shown). Optional electrode contact and quality determining circuit 92 is provided to assist the technician administering the test.

Noise reduction filter and stabilization circuit 93 comprises filtering and signal stabilization circuitry (such as signal baseline restoration).

Amplifier 94 amplifies the filtered signals from noise reduction filter and stabilization circuit 93. Amplifier 94 can comprise one or more stages of amplification, suitable for receiving weak physiological voltage or current signals (bioelectrical action potentials). The electrode signal amplifier has a suitable bandwidth, gain, and can be galvanically isolated from the following circuitry.

The signals can be processed in analog circuitry, but more commonly can be digitized by an analog to digital converter (ADC) 95. The ADC 95 digital outputs can then be transmitted to a computer 96, such as an embedded microcomputer, personal computer, or computer workstation, for signal processing. Data can be saved to nonvolatile memory (part of computer 96, not shown) for post processing, or processing can be by a real-time processor. And, finally the results of the test can be displayed as graphs and textual data on display 97.

Suitable digitization rates can be chosen for the muscle activity time scales of interest. Typically the digitization rate is established by the sampling rate of ADC 95. That rate can be controlled by computer 96 (timing link not shown) or by a separate timing circuit (not shown). Sampling rates can take into account Nyquist considerations, and filter designs. Over sampling can also be employed as needed to reduce errors caused by aliasing.

The time scales of interest in VISEMG waveform parameters can range across several orders of magnitude. For example during micturition, data records of from 3 to 4 minutes can be of interest. And there are sub-events of muscle contractions in the typically in the range of 10 to 30 seconds within the 3 to 4 minute records. The same VISEMG waveforms can also contain relatively high bandwidth signal information, such as relatively high frequency data reflecting muscle electrical activity on the order of milliseconds. It is less likely, although not impossible, that useful VISEMG signal bandwidth can extend to about 5 MHz. Therefore the bandwidth of interest for VISEMG signal acquisition is generally from 1 milliHertz (mHz) to 5 MegaHertz (MHz).

Useful filters 93 include broadband designs, covering the entire bandwidth of interest, or banks of narrow bands, or otherwise tailored filters for view selected spectral components of the action potentials. The filters can be any combination of analog filters at the input analog stages, or implemented in software, including firmware in the computer. Filters can have one or more poles and be of filter types including but not limited to simple R-C, Butterworth, Bessel, Chebychev, and elliptic. If implemented as analog filters, they can be passive or active filters. Other suitable filters include switched capacitor filters, or digital signal processing filters implemented on digital chips, DSP processors, microprocessors, or on other types of computers. Suitable digital signal processing techniques can include, but are not limited to, Fast Fourier Transforms (FFT), digital finite impulse response (FIR) and infinite impulse response (IIR) filters, joint time/frequency analysis, wavelet analysis techniques, and other signal processing methods or algorithms as known in the art.

VISEMG waveforms can be characterized strictly in the time domain, strictly in the frequency domain, or by a combination of the two. This characterization can be important as several of the action potentials can exhibit pulsed or burst activity. Furthermore, the bursts can include within a plurality of frequency components. Also, the frequency components comprised within a burst may vary from the beginning of the burst to the end of a particular burst. It can be advantageous to measure the mean frequency of the burst and the frequency at one or more points of time in the burst, including the beginning, middle and end of the burst. Bursts can occur at fixed and varying rates reflecting the movement of muscles including the bladder muscles of interest.

In time domain, waveform pulses can be isolated and characterized by rise time, fall time, pulse width, amplitude, full width half maximum (FWHM), and other time domain characterizations. Similarly non-linear pulse shapes may be identified and characterized as by root mean square (rms) values or otherwise pattern matching as to a sine wave, polynomial curve, or exponential shape. In the frequency domain, signal spectral analysis can be done.

VISEMG waveforms can be characterized by any combination of the above techniques. For example, some VISEMG waveforms comprise fast and slow components. Therefore, the same waveform representing a vector, or combination of vectors (the potential between two electrodes), can be subjected to two or more simultaneous methods of analysis to derive various components of the bladder muscle signal of interest on the different time scales.

Further it is anticipated that one or more action potentials, or combination of action potentials, can be further processed to remove unwanted signals. The abdominal vectors contain electrical information from other muscles than just the detrusor and the sphincter muscles. Other muscle groups may create measurable undesired signal components such as a residual signal from the heart muscle or more likely "noise" caused by involuntary movements of the bowel or abdominal wall muscles. Filtering of undesired bioelectrical signal components can be done by the use of reference patches (additional vectors) placed elsewhere on the body or by removing known interfering signal components by mathematical techniques.

Furthermore, analysis can include trends in bladder activity over time. The trends can also be displayed on the display. Predictions of future trends can also be made based on the trend data. Such predictions can be based on trend directions and slopes. Predictions can also be made based matching current trends to accumulated trend data from past subjects. A programmed computer, such as an expert system, can automatically perform the trend analysis.

The display can be any form suitable for displaying graphs and textual information, such as an LCD display, CRT display, printed display, or other alpha numeric display including, or combined with a graphics capable display.

Optional display formats include, but are not limited to, NI urodynamic graphs, NI urodynamic graphs with accompanying automatically generated bladder condition information, VISEMG waveforms, VISEMG waveforms with accompanying automatically generated bladder condition information, or automatically generated bladder condition information alone. As VISEMG waveforms become more widely accepted, the display option of NI urodynamic graphs may not be necessary. In this embodiment, the programmed computer can automatically generate bladder condition information based solely on the VISEMG waveforms. In this embodiment conversion software for converting VISEMG waveforms to NI urodynamic graphs is not needed.

The present invention can also be implemented in portable form. As a portable instrument, it can offer the opportunity to assess diurnal and nocturnal variations of various urological conditions in bladder activity at home (reality documentation). In one embodiment of the portable form, a battery operated portable diagnostic apparatus can include a nonvolatile memory such as a solid-state drive. The portable embodiment can have no displays, minimal displays, such as power and/or recording indicators, or some diagnostic display, including an LCD display showing waveforms and/or other diagnostic information. Where the portable form is used in a wireless environment, it can operate without internal nonvolatile data memory by transmitting the acquired signals to another computer in near real-time, or in real-time for further analysis.

In another embodiment, the diagnostic apparatus including conversion to NI urodynamic graphs can include communications equipment to update the conversion routines. New conversion software or firmware can then be downloaded into the diagnostic apparatus, as from the Internet, as they become available. Alternate modes of communications include Intranet, cable, telephone, satellite, and wireless. Or, updates can be performed using transportable media such as CDROM, floppy disk, portable magnetic storage media, portable RAM drives, portable hard drives, and solid state drives.

Figure 10:
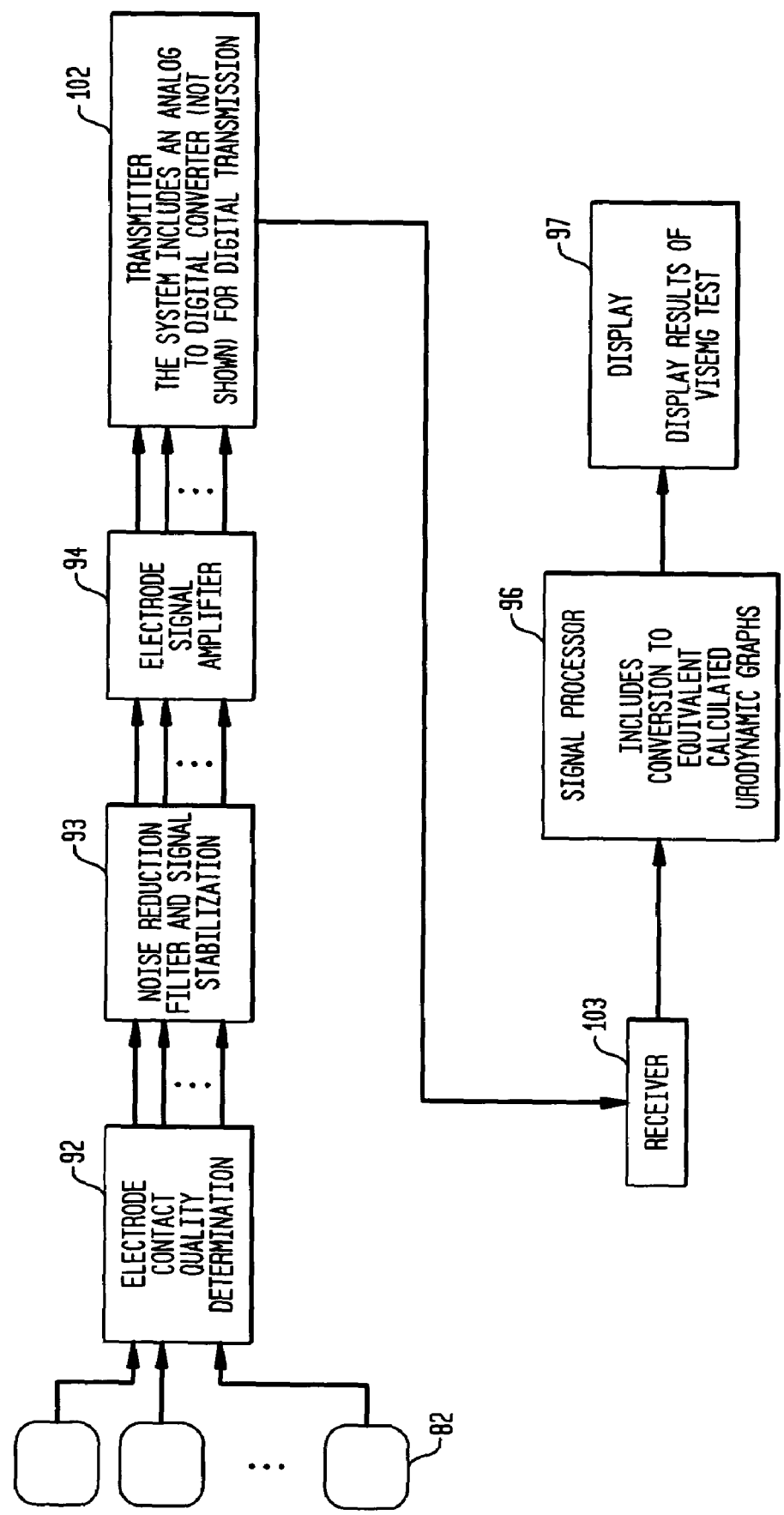
FIG. 10 shows an electronic block diagram of an embodiment of the apparatus where the front-end electronics is remotely located from the signal processing components.

In anther embodiment as shown in FIG. 10, the diagnostic apparatus can operate in the vicinity of the patient, but transfer and/or transmit the results of the VISEMG diagnostic testing to a remote location for a medical diagnosis by a medical professional. Transmitter 102 communicates the signals from amplifier 94 to a remote location. Where the transmission is digital, an analog to digital converter (not shown) can be used to digitize the signals. Receiver 103 receives the signals. The processor 96 processes the signals as previously described. In this case, the apparatus located with the patient need only include the front-end data-acquisition electronics needed to acquire the VISEMG signals. In this embodiment, the remaining apparatus to convert the data to the NI urodynamic graphs and/or to display the VISEMG waveforms and automatic computer generated bladder diagnosis information can be located on another computer in another location. Communications between the front-end electronics from transmitter 102 and receiver 103, coupled to the remainder of processing apparatus, can be made by such methods as acoustic, fiber (optics), infra-red (IR), wireless (RF), cable, Ethernet, intranet, or the Internet. It is further understood that both transmitter 102 and receiver 103 could be transceivers, thus allowing two-way communications to the patient's remote location. Furthermore, information can be shown on a display at the patient's location, ranging in complexity from simple messages regarding the quality of the electrode placements (location or coming loose) to a full copy of the processed data screens.

Also, while an important aspect of the invention is the computer signal processing and processed diagnostic information, it may be advantageous for the practitioner to also hear the signals. Therefore some embodiments of the invention can include audio amplifiers and speakers. The sounds can be direct reproductions of the amplified signals from the electrodes. The sounds can also include other audio information, ranging from beeps associated with user interfaces, such as key pads, to alarms, synthesized voice messages on equipment status, such as loose electrodes, summary diagnostic information for the diagnostician, and/or synthesized waveform data, reflecting analyzed and processed signals.

III. TRADITIONAL URODYNAMICS COMPARED TO VISEMG AND THE CONVERSION SOFTWARE

Traditional Urodynamics compared to VISEMG:

In the traditional Urodynamics a series of mechanical tests, such as bladder and abdominal pressures and flow measurements, are the most significant parameters recorded. In addition electromyographic (EMG) electrical signals (action potentials) from the striated muscles of the external sphincter and the pelvic floor musculature, are typically recorded in conjunction with traditional urodynamics. The traditional urodynamics are invasive (require bladder and rectal catheterization), are done only in an office or clinic setup (i.e. artificial environment, thus are subject to artificial data) and may reflect the outcome of intrinsic electrical processes within the muscularity of the bladder and the urethra, without disclosing these electrical events that lead to these mechanical and pressures changes. Thus in the clinical case of overactive bladder, traditional urodynamics will identify abrupt pressure elevations and changes within the bladder cavity.

However, direct electrophysiological recording of electrical signals from the smooth muscle of the bladder (detrusor) may reveal electric activity that stimulates the overactive detrusor muscle, thus resulting in these pressure elevations and changes. This data obtained from direct detrusor and sphincteric electrophysiological recordings can for example, potentially identify a pacemaker that initiates the electromuscular activity, the propagation of these electric waves within the bladder and their correlation to the ultimate bladder pressure changes or its outlet. Therefore obtaining electromyographic signals from the smooth muscle of the detrusor and the internal sphincter in normal subjects and those with lower urinary symptoms and concomitantly comparing them with traditional urodynamic evaluation, can provide information with regard to the underlying pathophysiology. And as in this example, it can also assist in treating these conditions.

By contrast, VISEMG testing including measurements of the action potentials caused by the detrusor muscle, and the internal and the external sphincters, is solely an electrical measurement. The conversion of VISEMG waveforms to NI urodynamic waveforms is largely a calculated conversion of electrical signals to graphs representing mechanical processes (urodynamics). Since urologists are most familiar with, and most confident in diagnosis by urodynamics, VISEMG signals, including detrusor signals, can be directly converted in real time, or near real time, to the NI urodynamic graph displays for the convenience of the clinician. It must be emphasized that the conversion to NI urodynamic graphs is a tool for interpretation and understanding of VISEMG waveforms. The conversion is not necessary for bladder diagnosis, which can be done directly from the VISEMG waveforms.

Figure 11:
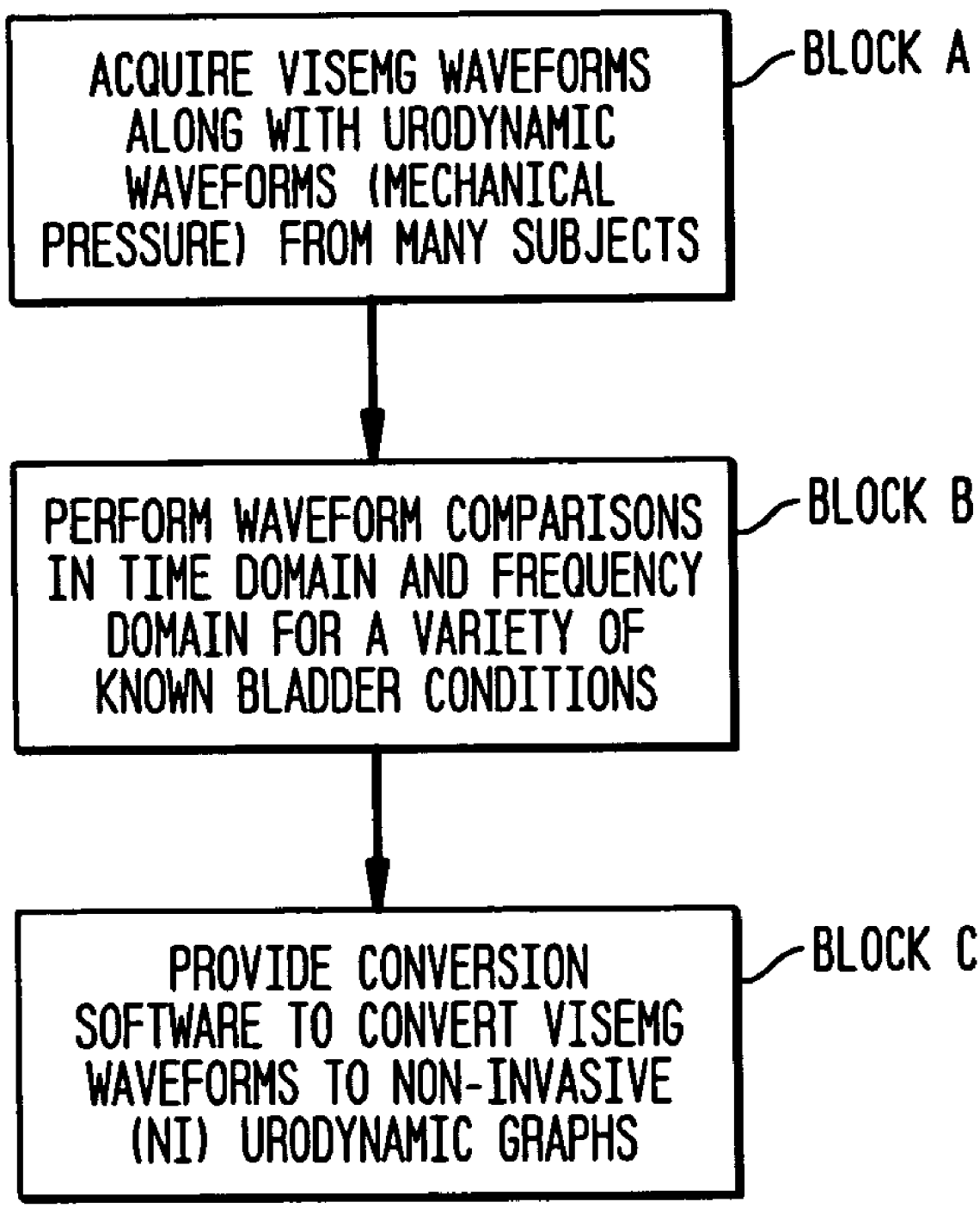
FIG. 11 is a block diagram showing a method to provide the conversion software.

The conversion software:

An exemplary method for generating the conversion software to convert from VISEMG waveforms to NI urodynamic graphs is shown in FIG. 11. Simultaneous, or near simultaneous VISEMG waveforms and traditional urodynamic tests are done on a number of patients in one or more studies (Block A). The traditional urodynamic graphs are compared to the VISEMG waveforms in time domain and in frequency domain (Block B) for a range of known bladder conditions. The conversion software is then written and or configured to convert VISEMG waveforms to NI urodynamic graphs (Block C).

The conversion software can be established based on one comprehensive test. Or, as envisioned here, it can be continuously updated at either regular intervals (as twice per year), or as significant advances are made in further understanding the relationships between VISEMG waveforms and NI urodynamic graphs. Further knowledge can come from additional dedicated studies.

It is also envisioned according to one embodiment of the invention that VISEMG apparatus can relay patient test data to one or more central repositories where VISEMG waveforms, optionally in conjunction with clinician comments, can be reviewed and further contribute towards the understanding of VISEMG waveforms.

It is understood that the above-described embodiments are illustrative of only a few of the many possible specific embodiments, which can represent applications of the invention. Numerous and varied other arrangements can be made by those skilled in the art without departing from the spirit and scope of the invention.

APPENDIX I: ADDITIONAL EXEMPLARY DISPLAY SCREENS

Figure 12:
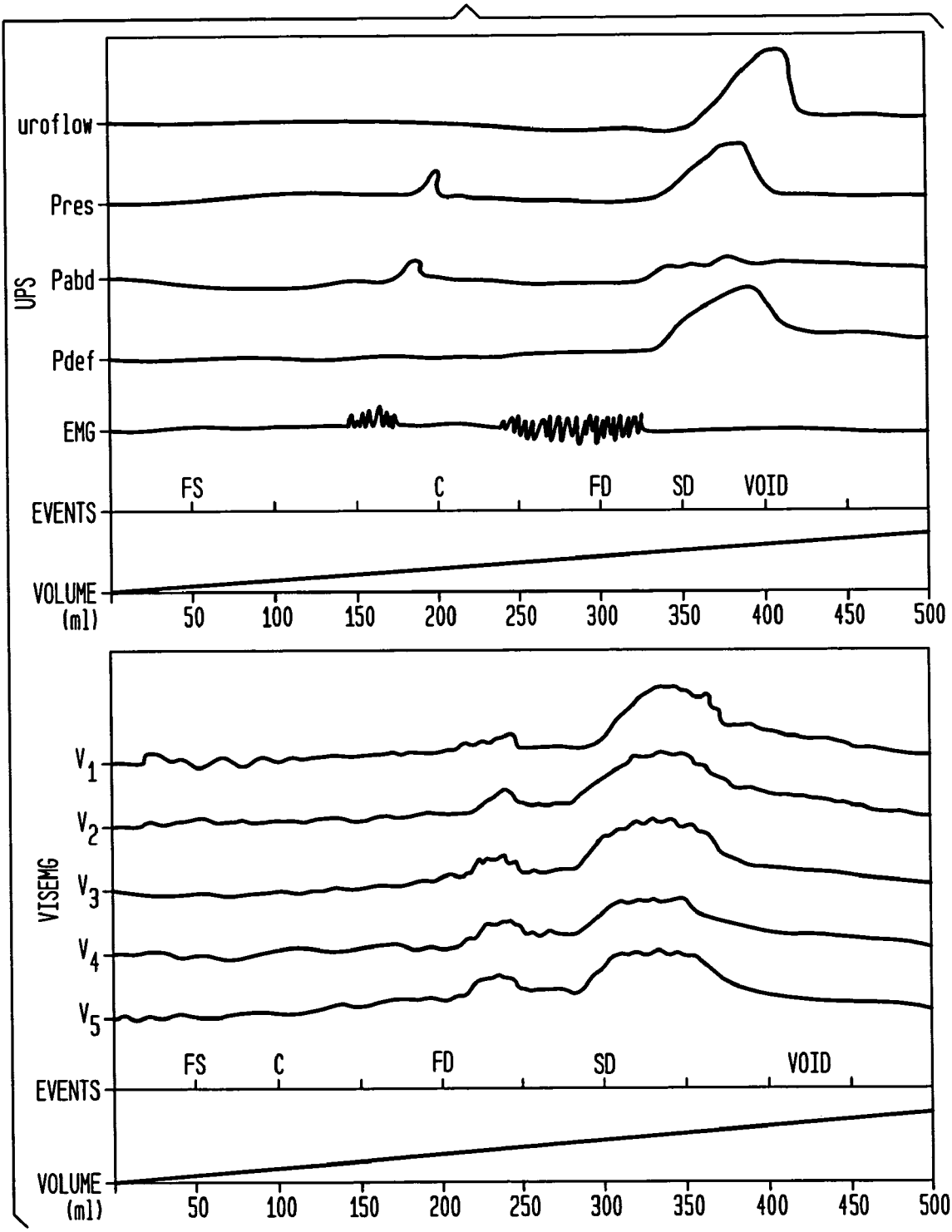
FIG. 12 shows one embodiment of a display screen for a normal bladder.
Figure 13:
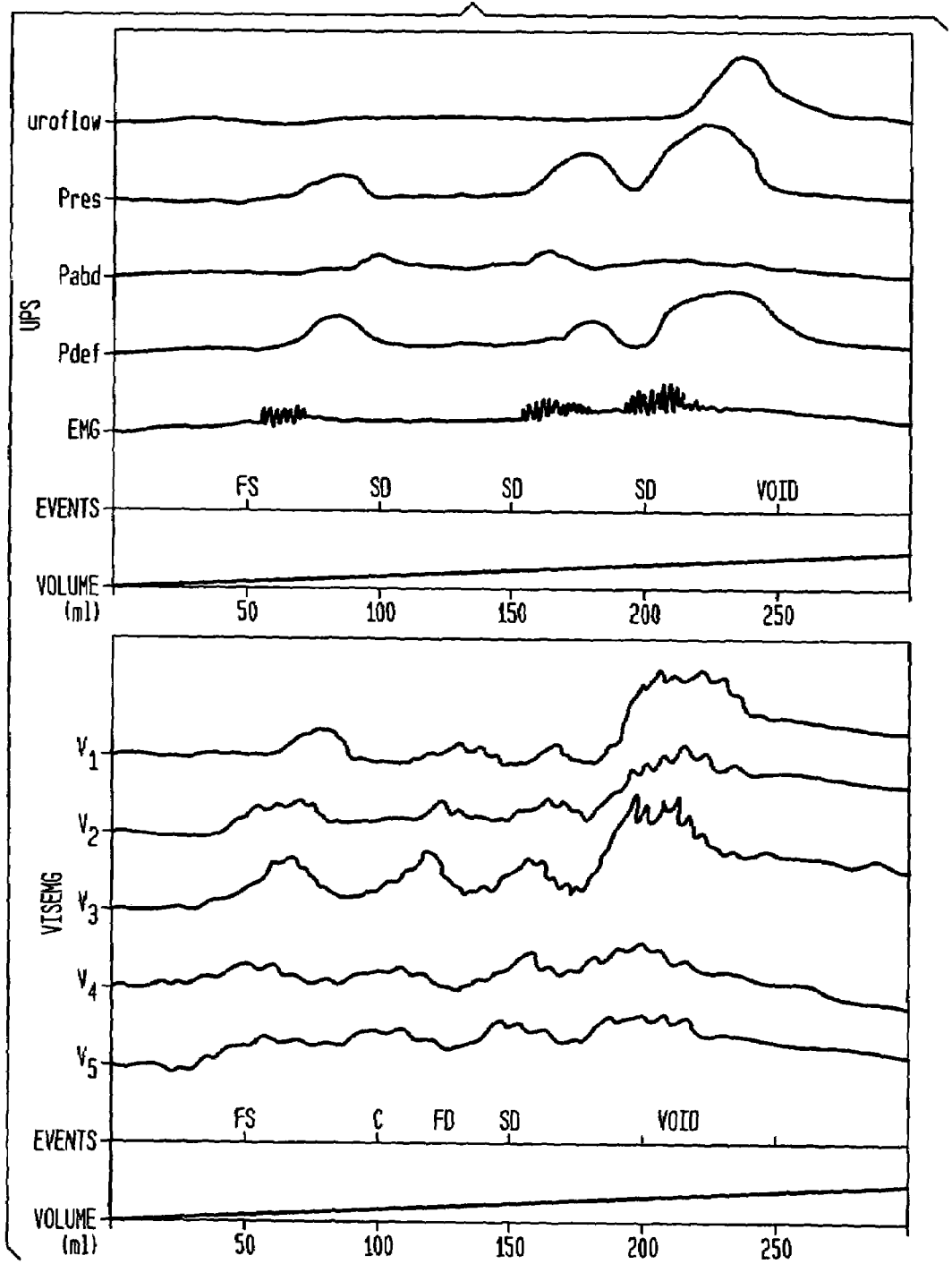
FIG. 13 shows one embodiment of a display screen for an overactive bladder condition.
Figure 14:
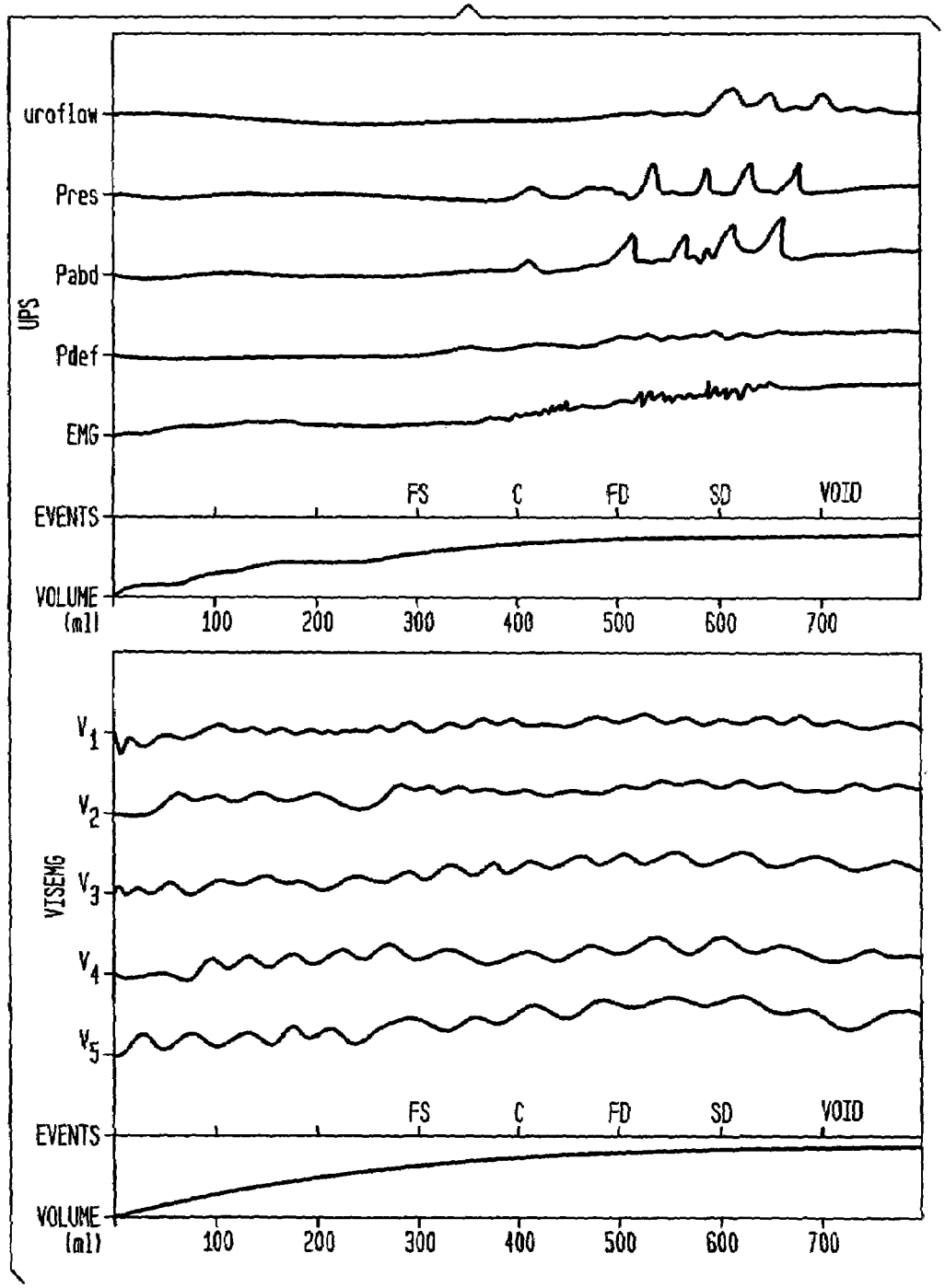
FIG. 14 shows one embodiment of a display screen for a contractile (paralyzed) detrusor.
Figure 15:
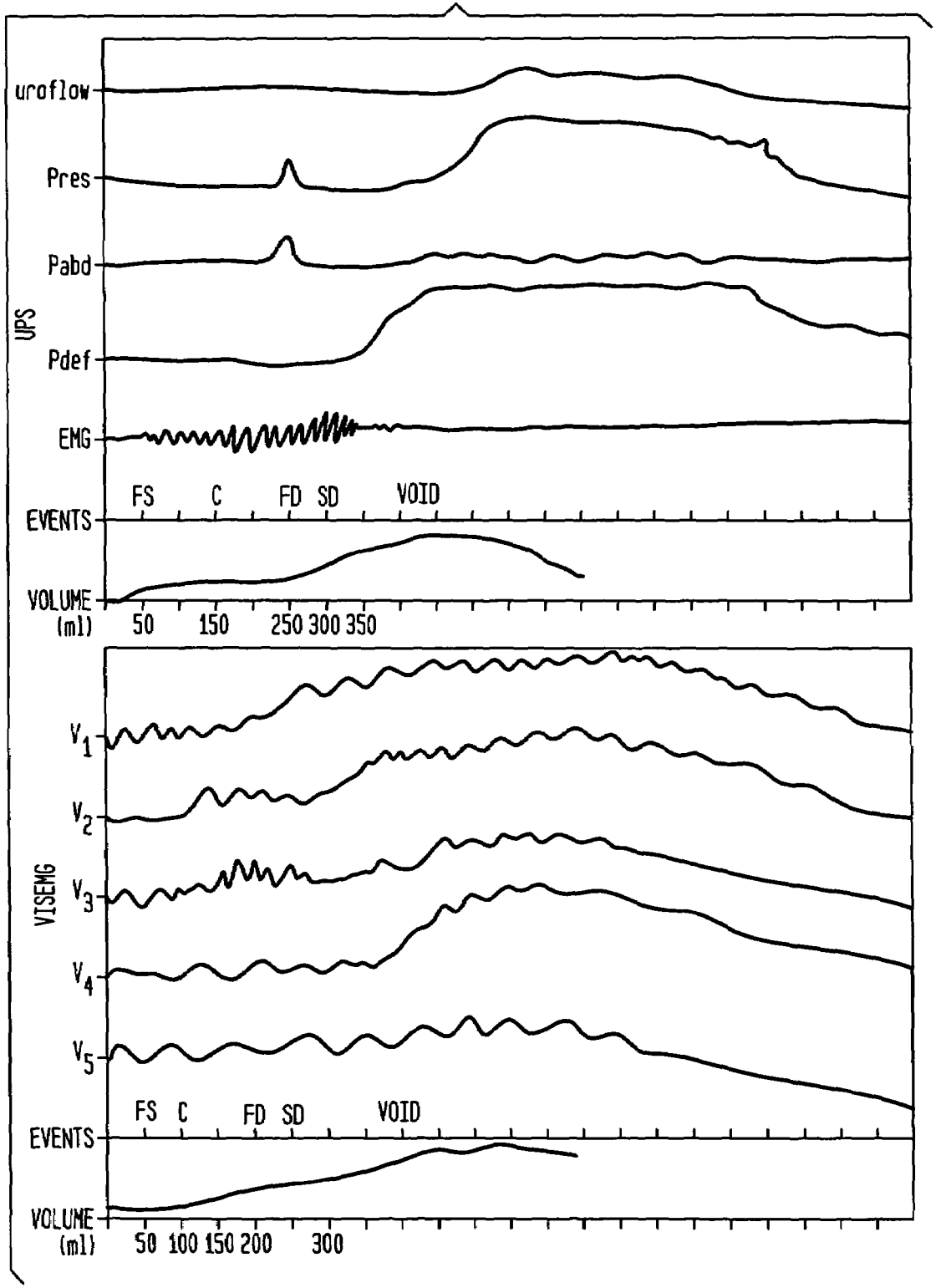
FIG. 15 shows one embodiment of a display screen for a bladder outlet obstruction.

Exemplary display screens according to one embodiment of the inventive apparatus are shown in FIGS. 12–15. FIG. 12 shows a display screen for a normal bladder, FIG. 13 shows a display screen for an overactive bladder condition, FIG. 14 shows a display screen for an acontractile (paralyzed) detrusor, and FIG. 15 shows a display screen for a bladder outlet obstruction. The urodynamic (UDS) graphs are the result of conversion by algorithm from the VISEMG waveforms. They are what a clinician would observe if traditional urodynamic tests were performed for the condition being viewed non-invasively by VISEMG inventive technique.

The events along the X-axis indicate marking of the patient's sensations where: FS is the first sensation during bladder filling, cough is a patient cough, FD is the first desire to urinate, and strong desire to urinate. Uroflows are shown in units of ml/sec, and Pres is the intravesical pressure, Pad is the intraabdominal pressure, Pdet is the Pres-Pad or the true detrusor pressure, EMG is the electromyography of the external sphincter, and volume is the volume in ml of the fluid infused into the bladder.

What is claimed:

1. A non-invasive method for diagnosing pathology in the bladder of a patient comprising the steps of:
    placing a plurality of electrodes on the patient;
    acquiring vesico internal sphincter electromyogram (VISEMG) waveforms from the electrodes on a patient;
    converting the VISEMG waveforms to non-invasive (NI) urodynamic graphs;
    displaying the results of the method; and diagnosing the condition of the bladder.

2. The method of claim 1 further comprising the step of assessing the condition of the bladder automatically based on the VISEMG waveforms.

3. The method of claim 1 wherein displaying the results comprises displaying the NI urodynamic graphs.

4. The method of claim 1 wherein displaying the results comprises displaying the VISEMG waveforms.

5. The method of claim 1 wherein displaying the results comprises displaying the diagnosis of bladder condition based on the VISEMG waveforms.

6. The method of claim 1 wherein placing the electrodes on the patient comprises placing a plurality of surface patches on the patient's abdomen including the suprapubic and perineal regions.

7. An apparatus for diagnosing bladder pathology from electromyographic (VISEMG) waveforms comprising:
    a plurality of surface electrodes;
    a plurality of input amplifiers for receiving electrical signals from VISEMG surface electrodes, each amplifier including at least one filter coupled to the amplifier for filtering each VLSEMG signal;
    an analog to digital converter (ADC) coupled to the amplifiers for sampling the analog signals and converting each sampled signal to a digital VISEMG waveform;
    a conversion software for converting VISEMG waveforms to non-invasive (NI) urodynamic graphs;
    a programmed computer to receive the digital signals and to convert them to NI urodynamic graphs; and
    a display to output the results of the VISEMG measurement useful to diagnose the condition of the bladder based on the VISEMG measurement.

8. The apparatus of claim 7 wherein the display further comprises user selectable display modes to display information selected from the group consisting of NI graphs, NI graphs and bladder condition based on the VISEMG waveforms, VISEMG waveforms, VISEMG waveforms and bladder condition based on the VISEMG waveforms, and NI graphs and VISEMG waveforms and VISEMG waveforms and bladder condition based on the VISEMG waveforms.

9. The apparatus of claim 7 wherein the display displays NI urodynamic graphs converted from the digital VISEMG waveforms.

10. The apparatus of claim 9 wherein the display further displays suspected bladder pathologies based on the VISEMG waveforms.

11. The apparatus of claim 7 wherein the display displays a representation of the digital VISEMG waveform.

12. The apparatus of claim 7 wherein the display further displays suspected bladder pathologies based on the VISEMG waveforms.

13. The apparatus of claim 7 wherein the apparatus is portable.

14. The apparatus of claim 7 wherein the conversion software is updated from a media selected from the group consisting of CDROM, floppy disk, portable magnetic storage media, portable RAM drives, portable hard drives, and solid state drives.

15. The apparatus of claim 7 wherein the conversion software is updated from an update server by a communications mode selected from the group consisting of Internet, Intranet, cable, telephone, satellite, and wireless.

* * * * *